US010184918B2

(12) United States Patent
Yamazaki

(10) Patent No.: US 10,184,918 B2
(45) Date of Patent: Jan. 22, 2019

(54) GAS-SPOUTING LIQUID-SAMPLE INJECTOR AND INJECTION CONTAINER FOR THE SAME

(71) Applicant: SHIMADZU CORPORATION, Kyoto-shi, Kyoto (JP)

(72) Inventor: Tomoyuki Yamazaki, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 286 days.

(21) Appl. No.: 15/287,829

(22) Filed: Oct. 7, 2016

(65) Prior Publication Data

US 2018/0100835 A1    Apr. 12, 2018

(51) Int. Cl.
G01N 30/30  (2006.01)
G01N 30/80  (2006.01)
B01D 15/24  (2006.01)

(52) U.S. Cl.
CPC ............ *G01N 30/30* (2013.01); *G01N 30/80* (2013.01); *B01D 15/247* (2013.01)

(58) Field of Classification Search
CPC ......... G01N 1/2258; G01N 1/22; G01N 1/24; G01N 1/20; G01N 1/286; G01N 1/10; G01N 23/2204; G01N 1/12; G01N 1/16; G01N 1/2273; G01N 30/02; G01N 30/32; G01N 30/461; G01N 30/34; G01N 30/36; G01N 33/0006; G01N 33/2823; B01L 3/505; B01L 3/508; B01L 3/021; B01L 3/0275; B01L 3/0279; F17C 6/00; B01D 15/24

USPC ...... 73/863.11–863.12, 863, 864.91, 864.01, 73/864, 61.52, 61.55, 61.56, 61.59; 210/635, 656, 96.1, 101, 143, 198.2

See application file for complete search history.

(56) References Cited

U.S. PATENT DOCUMENTS 3,011,336 A * 12/1961 Weiss ................... G01N 1/2202
73/863.12
2002/0043215 A1 * 4/2002 Yoshioka ............. B01D 1/0082
118/715

(Continued)

FOREIGN PATENT DOCUMENTS

| JP | 2003-149217 A | 5/2003 |
| WO | 2009/044425 A1 | 4/2009 |
| WO | 2009/044426 A1 | 4/2009 |

(Continued)

*Primary Examiner* — John Fitzgerald
*Assistant Examiner* — Truong D Phan
(74) *Attorney, Agent, or Firm* — Sughrue Mion, PLLC

(57) ABSTRACT

Provided is a gas-spouting liquid-sample injector, for supplying a mist of liquid sample into a container, including: a sample introduction tube having an outer tube for a nebulizer gas and an inner tube for a liquid, the inner tube having a projecting section protruding from the lower end of the outer tube; a branch tube provided in the container, having a main line allowing an insertion of the sample introduction tube and a bypass line branched from the main line; an inlet portion provided at the upper end of the main line, for making gas-tight contact with the lower end of the outer tube; an outlet portion provided at the lower end of the main line, for making gas-tight contact with the outer circumferential surface of the inner tube; and a blower tube extending from the lower end of the bypass line toward an area below the outlet portion.

6 Claims, 8 Drawing Sheets

(56) References Cited

U.S. PATENT DOCUMENTS

2002/0144949 A1* 10/2002 Berger .............. B01D 11/0203
                                                          210/656
2010/0300627 A1* 12/2010 Kono .................... B01D 15/24
                                                          159/48.1

FOREIGN PATENT DOCUMENTS

| WO | 2009/044427 A1 | 4/2009 |
| WO | 2009/044428 A1 | 4/2009 |

\* cited by examiner

Fig. 5A

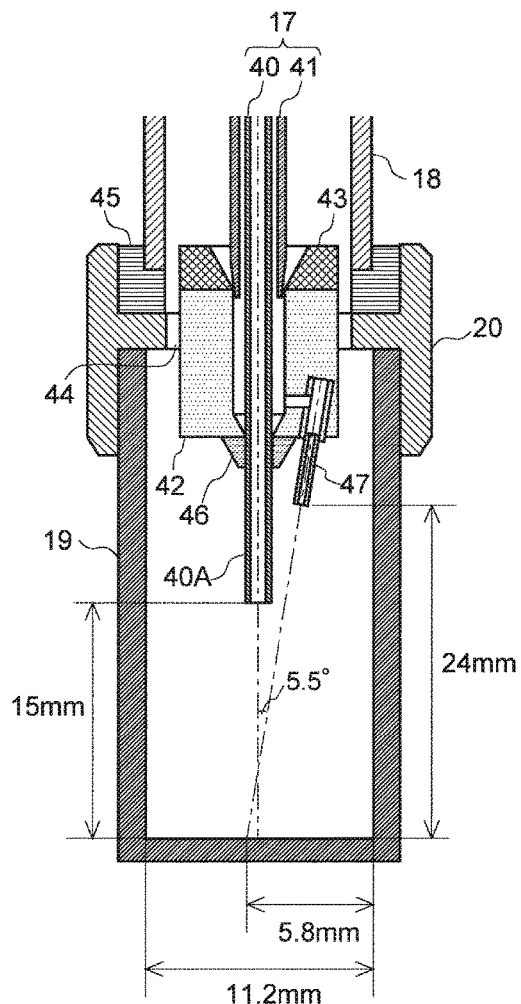

Fig. 5B

| | Symbol | Unit | Value | |
|---|---|---|---|---|
| Gas Flow Rate | Q | (L/s) | 0.026666667 | Gas flow rate = 1.6 L/M |
| Tube Inner Diameter | d | (m) | 0.001 | Gas nozzle, inner diameter = 1 mm |
| Mean Velocity | v | (m/s) | 33953.05453 | Substituted into a formula |
| Kinetic Viscosity | λ | (m2/s) | 0.00001512 | Physical property value for nitrogen gas (at room temperature) |
| | Re | | 2245572 | Critical Reynolds number ; Rec=2320 |
| | | | Turbulent flow | Flow is turbulent if Re>Rec, or laminer if Re<Rec. |

Reynolds number Re = v d / λ

Fig. 6A
Fig. 6B
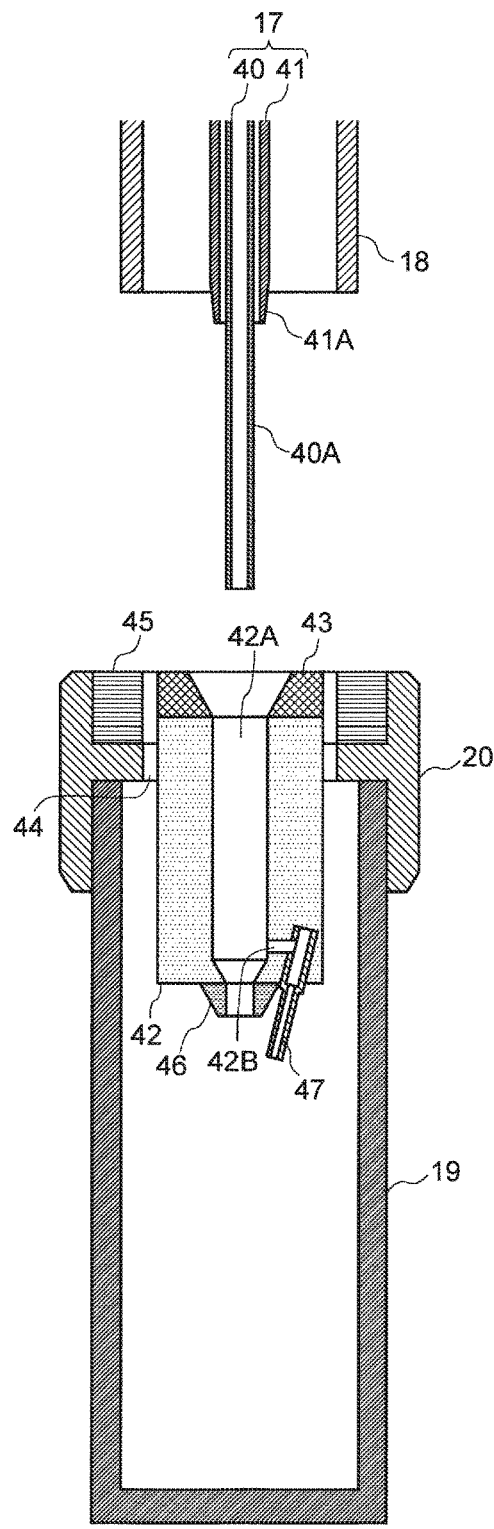
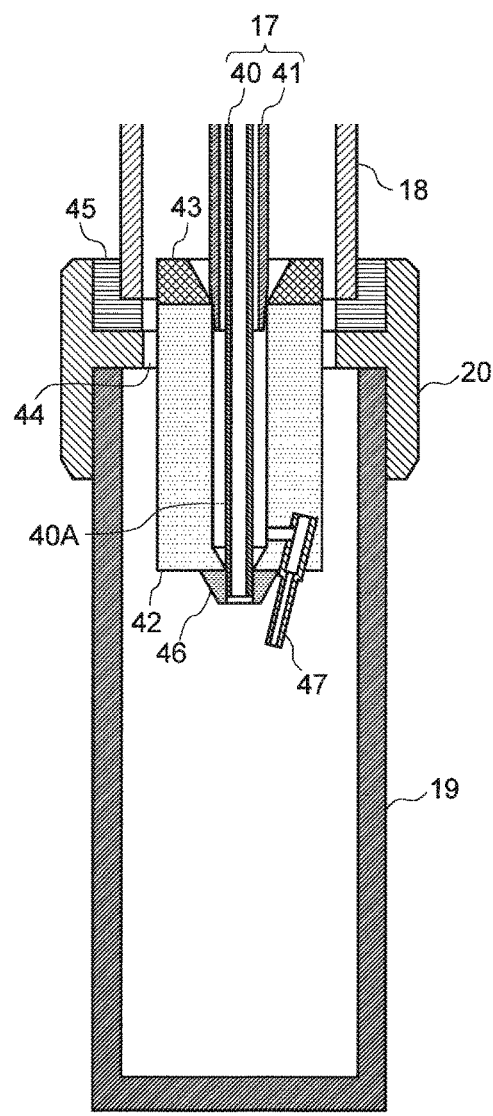

GAS-SPOUTING LIQUID-SAMPLE INJECTOR AND INJECTION CONTAINER FOR THE SAME

TECHNICAL FIELD

The present invention relates to a gas-spouting liquid-sample injector for injecting a sample into an injection container while nebulizing the liquid sample by spouting a stream of gas onto it, as well as an injection container used for such an injector. The injection container and the gas-spouting liquid-sample injector can be suitably used in a preparative separation-purification system for individually purifying and collecting one or more components in a solution after those components are separated from each other by using a liquid chromatograph.

BACKGROUND ART

For example, in pharmaceuticals fields, a preparative separation-purification system employing a liquid chromatograph is used for such tasks as collecting a sample to be stored in a library. In a system disclosed in Patent Literature 1, the target components (compounds) in a sample solution are temporally separated by a liquid chromatograph. The separated target components are individually introduced into separate trap columns and temporarily captured in those columns. Subsequently, a solvent is passed through each trap column to elute the component captured in the column. The obtained solution containing the target component is collected in a container. After that, a drying process for removing the solvent and collecting the target component in a solid form is performed.

In general, the drying process is performed by heating the collected solution. However, in order to avoid alteration of the target component, the process must be performed at a considerably low temperature. Therefore, the process may require several hours, or even up to 24 hours, depending on the component. This drying process consumes the largest amount of time in the preparative separation-purification process. Accordingly, in order to reduce the entire processing time, it is essential to shorten the period of time for the drying process.

A method for solving the previously described problem is disclosed in Patent Literatures 2-5, in which the vaporization of a solvent from a solution containing a target component is promoted by nebulizing the solution by spouting a stream of gas (e.g. air or nitrogen) onto the solution while dropping the solution into a collection container.

A typical procedure of the drying process according to the method described in Patent Literatures 2-5 (which is hereinafter called the "gas-spouting vaporization-drying process") is hereinafter described using FIGS. 8A-8D. The preparative separation-purification system in FIGS. 8A-8D includes a temperature-control block 54 for heating a collection container 53 to a predetermined temperature, a solution introduction tube 50 for introducing a solution into the collection container 53 placed in the temperature-control block 54, and a sealed tube 55 for discharging the gas introduced into the collection container 53 and the solvent vaporized within the same container 53, without allowing the gas and the solvent to leak to the outside of the system. The solution introduction tube 50 and the sealed tube 55 are integrally formed. The solution introduction tube 50 has a double-tube structure having an inner tube 50A through which the solution flows and an outer tube 50B through which the nebulizer gas flows. The collection container 53 includes a collection container body 51 and a cover part 52, with a hole formed at its center, to be attached to the upper opening of the container body 51. A doughnut-shaped cushion 52A is fitted in the upper portion of the cover part 52.

In the gas-spouting vaporization-drying process, the solution introduction tube 50 is lowered and inserted into the collection container 53 through the central hole of the cover part 52 and the cushion 52A. With this motion, the sealed tube 55 also moves downward, with its tip compressing the cushion 52A. The tip of the sealed tube 55 comes in tight contact with the cushion 52A and creates a gas-tight connection between the collection container 53 and the sealed tube 55. After that, the solution and the nebulizer gas are supplied to the inner tube 50A and the outer tube 50B, respectively. Being sheared by the stream of the nebulizer gas spouted from the outer tube 50B, the solution dropped from the tip of the inner tube 50A is broken into fine droplets (mist) and adhered to the inner wall of the collection container 53. Since the collection container 53 is previously heated by the temperature-control block 54, the solvent in the droplets adhered to the inner wall of the container turns into vapor, leaving behind the target component (solute) in a powdered form. The nebulizer gas introduced into the collection container 53 and the solvent vaporized within the same container 53 are discharged through the sealed tube 55.

CITATION LIST

Patent Literature

Patent Literature 1: JP 2003-149217 A
Patent Literature 2: WO 2009/044425 A1
Patent Literature 3: WO 2009/044426 A1
Patent Literature 4: WO 2009/044427 A1
Patent Literature 5: WO 2009/044428 A1

SUMMARY OF INVENTION

Technical Problem

The conventional preparative separation-purification system having the double-tube structure as shown in FIGS. 8A-8D provides a high level of drying performance. However, in some cases, the solution dropped from the inner tube is broken into sizes that are too small by the shearing force of the gas stream from the outer tube, with the result that the target component left behind in a powdered form on the inner wall of the collection container becomes in the form of extremely small particles. If such a powder with extremely small particle sizes is deposited on the inner wall of the collection container and forms a thin layer, it is difficult to scrape the powder from the wall surface and take it out of the collection container.

The problem to be solved by the present invention is to provide a gas-spouting liquid-sample injector for injecting a liquid sample into a specified type of container (which is hereinafter called the "injection container") while nebulizing the liquid sample by spouting a stream of gas onto it as in the previously described gas-spouting vaporization-drying process, with the injection container configured so that the liquid sample can be nebulized into particles with appropriate sizes. The present invention also provides an injection container for such an injector.

Solution to Problem

The present invention developed for solving the previously described problem is an injection container for a liquid-sample injector equipped with a sample introduction tube composed of an outer tube for a nebulizer gas and an inner tube for a liquid, the inner tube having a projecting section protruding downward from the lower end of the outer tube, the injection container configured to be supplied with a mist of liquid sample from the sample introduction tube, and the injection container including:

an injection container body with an upper opening;

a cover part to be attached to the opening;

a branch tube provided so as to penetrate the cover part, having a main line allowing an insertion of the sample introduction tube and a bypass line branched from the main line, the main line having an inner diameter larger than the outer diameter of the inner tube;

an inlet portion provided at the upper end of the main line, having a structure for making gas-tight contact with the lower end of the outer tube;

an outlet portion provided at the lower end of the main line, having a structure for making gas-tight contact with the outer circumferential surface of the inner tube; and a blower tube extending from the lower end of the bypass line toward an area below the outlet portion of the main line.

In the injection container for a gas-spouting liquid-sample injector according to the present invention, the cover part is provided with a branch tube. In the process of introducing a liquid sample into the injection container, the outer tube for a nebulizer gas comes in gas-tight contact with the inlet portion provided at the upper end of the main line of the branch tube. Simultaneously, the projecting section of the inner tube for a liquid comes in gas-tight contact with the outlet portion provided at the lower end of the main line of the branch tube. Therefore, the nebulizer gas supplied from the outer tube initially enters the main line of the branch tube and is subsequently diverted from the main line into the bypass line, to be eventually spouted from the blower tube provided at the lower end of the bypass line.

Since the blower tube is directed at an area below the outlet portion of the main line, the nebulizer gas spouted from the blower tube obliquely hits the dropped liquid sample. In the case of the conventional double-tube structure, since the liquid sample and the nebulizer gas flows coaxially, the liquid sample is exposed to the stream of the nebulizer gas over a long distance, so that the resulting mist will have an extremely small diameter. By comparison, in the branch-tube structure of the present invention, since the nebulizer gas obliquely hits the liquid sample, the liquid sample is exposed to the stream of the nebulizer gas over a shorter distance, so that the resulting mist will have a larger diameter. As will be explained in the embodiment, the particle size of the mist mainly depends on the position and direction of the tip of the blower tube (or more specifically, the distance from the tip of the blower tube to the liquid sample). Accordingly, it is possible to nebulize the liquid sample into an optimum particle size by appropriately changing the position and/or direction of the tip of the blower tube.

The gas-spouting liquid-sample injector according to the present invention developed for solving the previously described problem includes:

a sample introduction tube for supplying a liquid sample in a mist form into an injection container, the sample introduction tube composed of an outer tube for a nebulizer gas and an inner tube for a liquid, the inner tube having a projecting section protruding downward from the lower end of the outer tube;

a branch tube provided in the injection container, having a main line allowing an insertion of the sample introduction tube and a bypass line branched from the main line, the main line having an inner diameter larger than the outer diameter of the inner tube;

an inlet portion provided at the upper end of the main line, having a structure for making gas-tight contact with the lower end of the outer tube;

an outlet portion provided at the lower end of the main line, having a structure for making gas-tight contact with the outer circumferential surface of the inner tube; and a blower tube extending from the lower end of the bypass line toward an area below the outlet portion of the main line.

It is preferable that this gas-spouting liquid-sample injector additionally includes a heater for heating the injection container. By this system, the solvent contained in the droplets of the mist is quickly vaporized, leaving a powdered substance in the injection container. Since the gas-spouting liquid-sample injector according to the present invention produces mist with a larger diameter than the conventional device, the powder which remains after the vaporization of the solvent also has a larger particle size. As noted earlier, a powder having an optimum particle size can be obtained for each liquid sample (or depending on any other factor) by appropriately changing the position and/or direction of the tip of the blower tube.

Advantageous Effects of the Invention

The injection container for a gas-spouting liquid-sample injector according to the present invention is characterized by the branch tube and the blower tube which are provided in the cover part so as to obliquely spout a stream of gas onto a liquid sample being dropped. According to this configuration, the liquid sample is exposed to the gas stream over a short distance, so that the eventually obtained mist has a large diameter. Additionally, a powder having an optimum particle size can be obtained for each liquid sample (or depending on any other factor) by appropriately changing the position and/or direction of the tip of the blower tube.

BRIEF DESCRIPTION OF DRAWINGS

FIG. 1 is a configuration diagram showing the main components of a preparative separation-purification system using a gas-spouting liquid-sample injector according to one embodiment of the present invention.

FIGS. 2A and 2B are schematic vertical sectional views showing the configuration of the injection container used for the liquid-sample injector of the present embodiment, where FIG. 2A is an overall view of the container while FIG. 2B shows each part of the same container in a separated form.

FIGS. 3A and 3B are schematic vertical sectional views showing the relationship between the sample introduction tube (FIG. 3A) in the gas-spouting liquid-sample injector of the present embodiment and the branch tube (FIG. 3B) of the corresponding injection container.

FIGS. 4A and 4B are schematic vertical sectional views of the sample introduction tube and the injection container in the gas-spouting liquid-sample injector of the present embodiment, where FIG. 4A shows the state before the insertion of the sample introduction tube into the injection container and FIG. 4B shows the state after the insertion.

FIG. 5A is a diagram showing one example of the relevant dimensions of the injection container in the gas-spouting liquid-sample injector of the present embodiment, and FIG. 5B is a table showing the result of the calculation of the Reynolds number for a flow of nebulizer gas supplied using the injection container shown in FIG. 5A.

FIGS. 6A and 6B are schematic vertical sectional views of the sample introduction tube and the injection container in the gas-spouting liquid-sample injector according to one variation of the embodiment, where FIG. 6A shows the state before the insertion of the sample introduction tube into the injection container and FIG. 6B shows the state after the insertion.

FIG. 7A shows the state before the insertion of the sample introduction tube into the injection container and FIG. 7B shows the state after the insertion.

DESCRIPTION OF EMBODIMENTS

Figure 1:
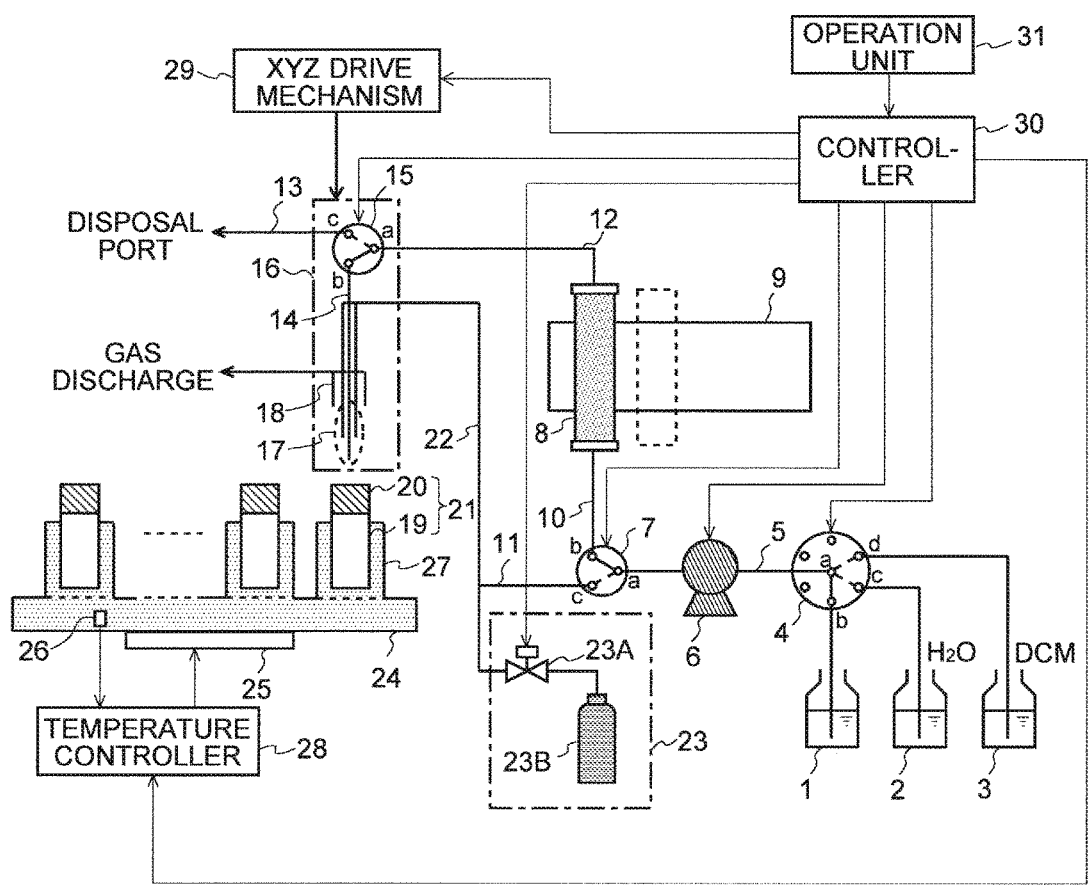

One embodiment of the gas-spouting liquid-sample injector according to the present invention is hereinafter described with reference to FIGS. 1-4B. FIG. 1 is a configuration diagram showing the main components of a preparative separation-purification system in which a gas-spouting liquid-sample injector according to the present embodiment is applied. As will be described later, this preparative separation-purification system is configured to handle a solution containing a target component previously obtained using a preparative separation liquid chromatograph (not shown). Alternatively, the system configuration may be modified in such a manner that the preparative separation liquid chromatograph is directly connected to the preparative separation-purification system and each fraction of the solution prepared by the liquid chromatograph is directly introduced into the preparative separation-purification system.

Figure 2A:
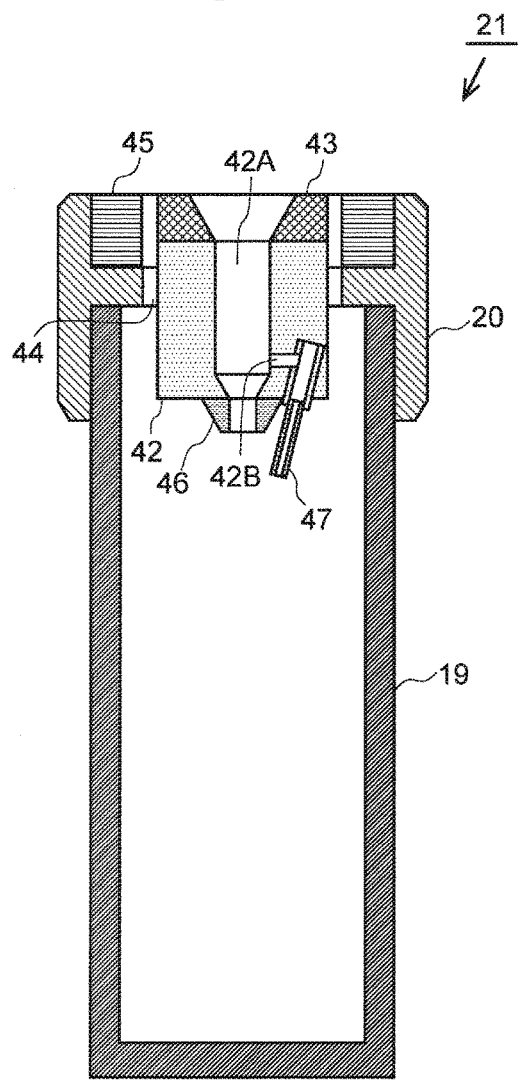
Figure 2B:
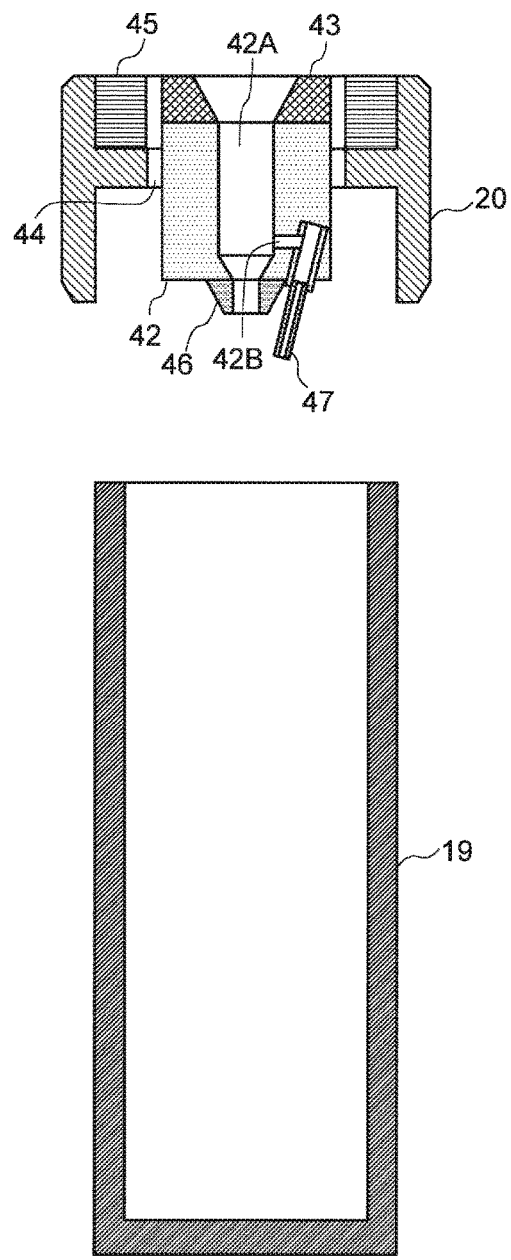
Figure 3A:
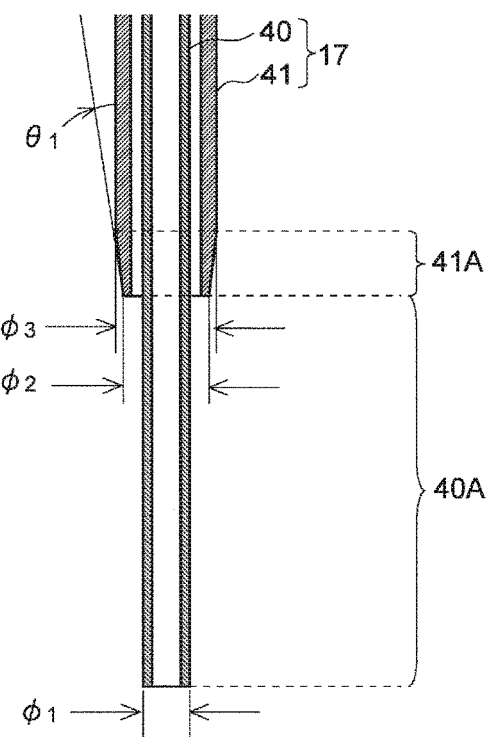
Figure 3B:
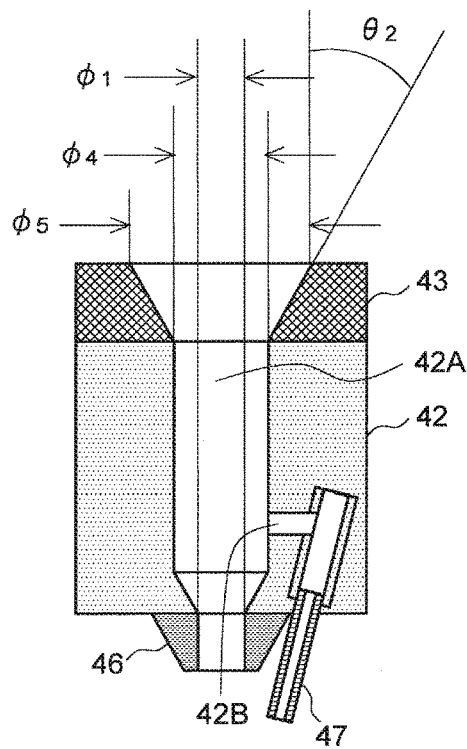
Figure 4A:
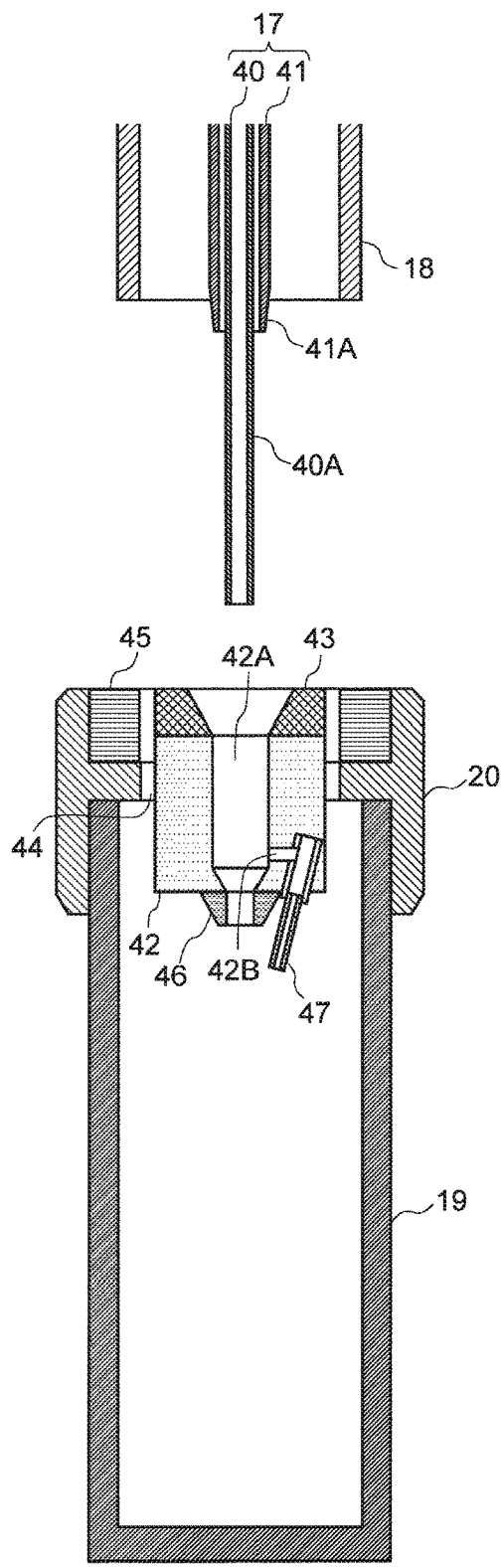
Figure 4B:
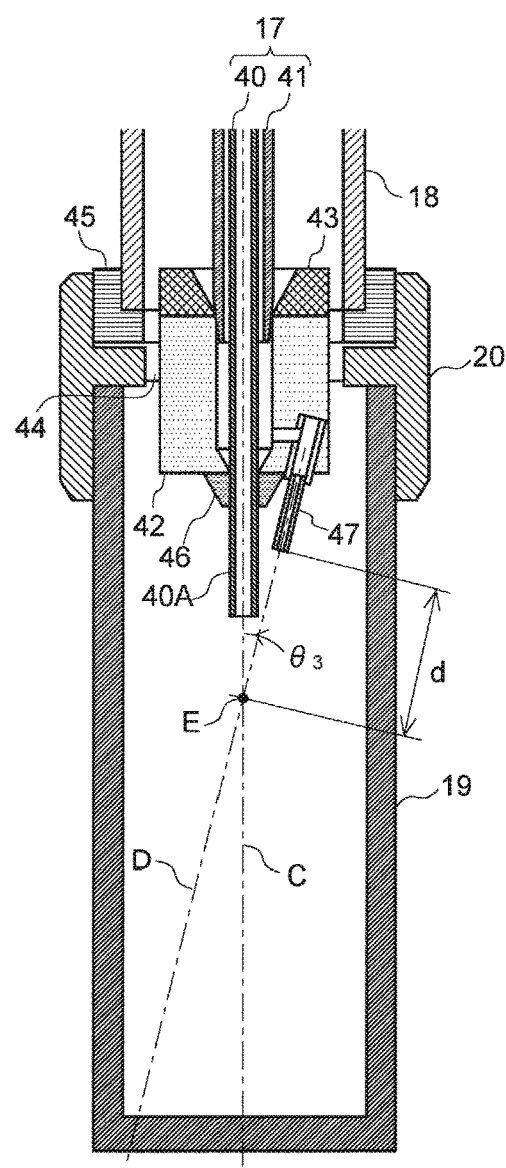

FIGS. 2A and 2B are schematic vertical sectional views of the injection container used for the gas-spouting liquid-sample injector of the present embodiment. FIGS. 3A and 3B are schematic vertical sectional views showing the relationship between the sample introduction tube in the gas-spouting liquid-sample injector of the present embodiment and the branch tube of the corresponding injection container. FIGS. 4A and 4B are schematic vertical sectional views showing the state of the sample introduction tube and the injection container in the gas-spouting liquid-sample injector of the present embodiment before and after the insertion of the sample introduction tube into the injection container.

In FIG. 1, a solution container 1 holds a previously obtained fraction of the solution containing a target component, with the mobile phase used in the chromatograph contained as the main solvent in the solution. A pure water container 2 holds pure water ($H_2O$), while an eluting solvent container 3 holds dichloromethane (DCM). A switching valve 4 is provided to switch the passage so as to allow one of the three kinds of liquids held in those containers 1, 2 and 3 to be selectively passed through a passage 5. A liquid-sending pump 6 for drawing and sending liquid at a preset flow rate is provided in the passage 5.

The exit end of the passage 5 is connected to port a of a switching valve 7. This switching valve 7 also has port b, to which a passage 10 leading to a trap column 8 packed with an adsorbent for capturing the target component is connected, and port c, to which a passage 11 leading to a passage 22 for a nebulizer gas (which will be described later) is connected. The switching valve 7 selectively connects either the passage 10 or 11 to the passage 5.

The trap column 8 is held in a column rack 9 in a substantially vertical position, with its inlet end (to which the passage 10 will be connected) directed downward and its outlet end (to which a passage 12, which will be described later, will be connected) directed upward. Although only one trap column 8 is shown in FIG. 1, a plurality of trap columns 8 can be arranged in the column rack 9, as indicated by the broken line in FIG. 1.

The passage 12, one end of which is connected to the outlet end of the trap column 8, has the other end connected to port a of a switching valve 15 included in a fraction collector head 16. The switching valve 15 also has port b, to which a passage 14 is connected, and port c, to which a passage 13 leading to a disposal port is connected. The switching valve 15 selectively connects either the passage 13 or 14 to the passage 12.

The fraction collector head 16 has a sample introduction tube 17 as well as a sealed exhaust tube 18 integrally formed around the sample introduction tube 17. This head can be driven in both horizontal and vertical directions by an XYZ drive mechanism 29 composed of a plurality of motors and other elements. The sample introduction tube 17 has an inner tube 40 connected to the passage 14 and an outer tube 41 connected to the passage 22 (the sample introduction tube 17 and the injection container 21 in FIG. 1 are shown in a simplified form; their specific configurations are shown in FIGS. 2A-4B). As will be described later, the inner tube 40 is supplied with a solution containing a target component through the passage 14, while the outer tube 41 is supplied with a nebulizer gas through the passage 22. The inner tube 40 has a projecting section 40A protruding downward from the lower end of the outer tube 41.

The injection containers 21, into which a solution will be injected, are individually held in the temperature-control blocks 27 on a container rack 24 which is provided with a heater 25 and a temperature sensor 26 (e.g. thermistor). The container rack 24 and the temperature-control blocks 27 are made of a highly heat-conductive material (e.g. aluminum) with its outer surface covered with a heat-insulating material (not shown) in order to prevent the loss of heat into the surrounding areas.

In order to facilitate the conduction of heat from the temperature-control blocks 27 to the injection containers 21, each container is in contact with the temperature-control block 27, at least on its bottom side. As a more preferable configuration, the circumferential side surface of the injection container 21 may also be in contact with the temperature-control block 27. A temperature controller 28, which is provided separately from the container rack 24, controls the heating current supplied to the heater 25 so that the temperature monitored with the temperature sensor 26 is maintained at the target temperature. By this system, the injection containers 21 are heated to and maintained at an appropriate temperature.

The fraction collector head 16 is driven via the XYZ drive mechanism 29 to be positioned above any one of the injection containers 21 held in the container rack 24 (FIG. 4A) and subsequently lowered.

The injection container 21 includes an injection container body 19 and a cover part 20 attached to the upper opening of the container body. As shown in FIGS. 2A-4B, the cover part 20 has the characteristic structure of the present invention, i.e. a branch tube 42 including a main line 42A allowing an insertion of the sample introduction tube 17 and a bypass line 42B branched from the main line 42A, with the main line 42A having an inner diameter $\varphi_4$ larger than the outer diameter $\varphi_1$ of the inner tube 40. An inlet portion 43 for guiding the sample introduction tube 17 into the main line 42A is provided at the upper end of the main line 42A of the branch tube 42. An outlet portion 46 whose inner diameter is equal to the outer diameter $\varphi_1$ of the inner tube 40 is provided at the lower end of the main line 42A. At the lower end of the bypass line 42B of the branch tube 42, a blower tube 47 is provided, which is directed at an area located below the outlet portion 46 and on the central line C of the main line 42A. Although the branch tube 42, inlet portion 43, outlet portion 46 and blower tube 47 in FIGS. 2A-4B are shown as separate parts, they may be formed as a single component, or only some of them may be provided as separate parts.

The cover part 20 has an exhaust opening 44 for discharging the nebulizer gas introduced into the injection container 21 and the solvent vaporized within the injection container 21, as well as a doughnut-shaped cushion 45 for improving the gas-tightness of the connection between the cover part 20 and the sealed exhaust tube 18.

Both the lower end portion of the outer tube 41 (indicated by numeral 41A in FIG. 3A) and the inner circumferential portion of the inlet portion 43 are tapered downward. Specifically, these two elements are designed to satisfy $\theta_2 > \theta_1$, where $\theta_1$ is the angle made by the outer circumferential surface of the lower end portion 41A and its central axis, while $\theta_2$ is the angle made by the inner circumferential surface of the inlet portion 43 and its central axis (FIGS. 3A and 3B). Additionally, the dimensions of the lower end portion 41A and the inlet portion 43 are designed to satisfy $\varphi_2 < \varphi_4 < \varphi_3 < \varphi_5$, where $\varphi_2$ and $\varphi_3$ are the diameters at the thinnest and thickest portions of the outer circumferential surface of the lower end portion 41A, while $\varphi_4$ and $\varphi_5$ are the diameters at the narrowest and widest portions of the inner circumference of the inlet portion 43.

Due to such a design of the dimensions and angles of the lower end portion 41A and the inlet portion 43, the sample introduction tube 17 is guided to the center of the inlet portion 43, with the outer tube 41 coming in gas-tight contact with the inlet portion 43. Furthermore, since the outer diameter of the inner tube 40 is equal to the inner diameter of the outlet portion 46, these two elements also come in gas-tight contact with each other (FIG. 4B).

With the downward motion of the sample introduction tube 17, the sealed exhaust tube 18 also moves downward, compressing the cushion 45 in the cover part 20. As a result, a gas-tight connection is created between the sealed exhaust tube 18 and the injection container 21 (FIG. 4B). In this state, a gas-spouting vaporization-drying process (which will be described later) is performed.

The drive mechanism may also be configured to drive the container rack 24 instead of driving the fraction collector head 16.

A gas supplier 23, which has a proportional valve 23A, a gas cylinder 23B and other components, sends a nebulizer gas to the outer tube 41 of the sample introduction tube 17 through the passage 22.

A controller 30, which includes a CPU and other components, automatically conducts the preparative separation-purification process by performing various control operations according to a preset program, such as the switching of the switching valves 4, 7 and 15, the operations of the liquid-sending pump 6 and the gas supplier 23 (flow rate or flow velocity), the setting of the target temperature for the temperature controller 28, as well as the driving of the fraction collector head 16 via the XYZ drive mechanism 29.

An operation unit 31 allows users to enter and set necessary information, such as the conditions for the preparative separation-purification.

The procedure of the gas-spouting vaporization-drying process by the preparative separation-purification system shown in FIG. 1 is hereinafter described. Initially, in order to capture the target component contained in a solution in the solution container 1 on the adsorbent in the trap column 8 and then dispose of the solvent (mobile phase) in the solution, the controller 30 operates the liquid-sending pump 6 so as to constantly supply liquid at a specific flow rate after setting the switching valve 4 to connect the solution container 1 (port b) and the passage 5 (port a), the switching valve 7 to connect the passage 5 (port a) and the passage 10 (port b), as well as the switching valve 15 to connect the passage 12 (port a) and the passage 13 (port c). The liquid-sending pump 6 draws the solution from the solution container 1 and introduces it into the trap column 8 through the passages 5 and 10. As a result, the target component in the solution is captured on the adsorbent in the trap column 8. The solution (mobile phase) with the target component removed is disposed of through the passages 12 and 13 to the disposal port.

After the solution in the solution container 1 is supplied to the trap column 8 for a predetermined period of time or by a predetermined quantity, the controller 30 turns the switching valve 4 to connect the pure water container 2 (port c) and the passage 5 (port a). Then, the liquid-sending pump 6 begins to draw the pure water from the pure water container 2 and introduces it into the trap column 8. By this process, unwanted water-soluble substances, such as the salts adhered to the adsorbent in the previous process of capturing the target component, are removed from the trap column 8. The supplied pure water replaces the mobile phase which is present in the trap column 8 immediately before the beginning the supply of the water. Ultimately, the trap column 8 becomes completely filled with the water. Due to the strong adsorption power, the target component captured on the adsorbent is barely eluted into the water. Therefore, at this stage, the target component remains in the captured state in the trap column 8.

Subsequently, the controller 30 drives the fraction collector head 16 via the XYZ drive mechanism 29 to a position above the branch tube 42 of a previously specified injection container 21 and subsequently lowers the same head 16 (FIG. 4B). Then, the controller 30 informs the temperature controller 28 of the target temperature and commands it to initiate the heating of the temperature-control block 27, whereby the temperature of the injection container 21 begins to increase. The target temperature can be set at a level approximately equal to or slightly higher than the boiling point of dichloromethane used as the solvent for eluting the target component, i.e. within a range from 40° C. to 45° C. Subsequently, the controller 30 turns the switching valve 4 to connect the eluting solvent container 3 (port d) and the passage 5 (port a). Then, the liquid-sending pump 6 begins to draw and introduce dichloromethane from the eluting solvent container 3 into the trap column 8.

As the dichloromethane is introduced into the trap column 8, the interface between the dichloromethane and the water which has already been present in the trap column 8 gradually moves upward, with the dichloromethane barely mixed with the water. In other words, the dichloromethane gradually accumulates from the bottom of the trap column 8, pushing the water upward. The pushed water flows over the outlet port at the upper end of the trap column 8 and is guided through the switching valve 15 and the passage 13 to the disposal port. Meanwhile, due to the strong elution power of the dichloromethane, the target component captured in the trap column 8 is eluted into the dichloromethane accumulated in the same column 8.

After the dichloromethane in the eluting solvent container 5 is supplied to the trap column 8 for a predetermined period of time or by a predetermined quantity, and the water is thereby completely removed from the trap column 8, the switching valve 15 is turned from the passage 13 (port c) to the passage 14 (port b) to initiate the preparative separation of the target component. The controller 30 also commands the gas supplier 23 to initiate the supply of nitrogen gas (or other kinds of inert gas). The nebulizer gas sent from the gas supplier 23 is introduced through the passage 22 and the outer tube 41 into the main line 42A of the branch tube 42. The inlet portion 43 provided at the upper end of the main line 42A is sealed with the lower end 41A of the outer tube 41, while the outlet portion 46 provided at the lower end of the main line 42A is sealed with the outer circumferential surface of the inner tube 40. Therefore, the nebulizer gas introduced into the main line 42A is diverted into the bypass line 42B and begins to be spouted from the blower tube 47. Meanwhile, the solution sent from the trap column 8, i.e. the dichloromethane containing the target component, flows through the passages 12 and 14, to be eventually dropped from the lower end of the inner tube 40 of the sample introduction tube 17. As noted earlier, the blower tube 47 is designed to be directed toward the central line C of the main line 42A. Therefore, the nebulizer gas spouted from the blower tube 47 hits the solution dropped from the inner tube 40, breaking the solution into mist by the shearing force.

In the injection container 21 of the present embodiment, unlike the conventional one, the solution and the nebulizer gas do not flow coaxially. Therefore, the solution is exposed to the nebulizer gas over a shorter distance, so that the resulting mist will have a larger particle size. Increasing the distance between the point E at which the solution is sheared (i.e. the point of intersection of the central line C and the straight line D indicating the direction of the blower tube 47) and the tip of the blower tube 47 makes the nebulizer gas more dispersed and less powerful, which similarly results in a larger particle size of the mist. Accordingly, the particle size of the obtained mist can be changed by appropriately adjusting the distance d from the tip of the blower tube 47 to the sharing point E and/or the angle $\theta_3$ made by the central line C and the straight line D. For this purpose, for example, the cover part 20 may have a structure with the position and/or angle of the tip of the blower tube 47 freely variable. It is also possible to prepare a plurality of cover parts 20 which vary in the position and/or angle of the tip of the blower tube 47. In this manner, the gas-spouting vaporization-drying process can be performed with an appropriate particle size of the mist depending on the particle size of the powder to be obtained or depending on the kind of sample.

The injection container 21 is maintained at an approximately equal temperature to the boiling point of dichloromethane by the heat conducted from the temperature-control block 27 using the heater 25 as the heat source. Therefore, when the fine droplets of the solution are adhered to the inner circumferential wall or inner bottom wall of the injection container 21, the solvent (dichloromethane) in the droplets immediately turns into vapor, leaving behind the target component in a powdered form. In this manner, the powder of the target component is deposited on the inner circumferential wall and inner bottom wall of the injection container 21. Meanwhile, the nebulizer gas introduced into the injection container 21 as well as the vapor of the solvent are discharged through the sealed exhaust tube 18 to the outside of the injection container 21.

After the previously described processes have been completed, the fraction collector head 16 is elevated. If there is another target component to be processed into powder, the fraction collector head 16 is moved to the position where the next injection container 21 is located, and the processes are similarly performed.

In the previously described gas-spouting vaporization-drying process of the present embodiment using the preparative separation-purification system shown in FIG. 1, the solute may be deposited at the tip of the inner tube 40 of the sample introduction tube 17, developing along the outer wall of the inner tube 40 in the middle of the gas-spouting vaporization-drying process. To prevent this situation, the inner tube 40 should preferably be made of a resin material categorized as polytetrafluoroethylene (PTFE), such as Teflon®. A PTFE resin has a low degree of wettability and does not easily allow the solution to climb on the outer wall of the inner tube 40 from the tip of the same tube due to the surface tension. For the same reason, the branch tube 42 should also be made of a PTFE resin material.

The exit port of the blower tube 47 should preferably have an elongated rectangular shape. By this configuration, the nebulizer gas spouted from the blower tube 47 is shaped into a broad stream which covers a wide area.

Furthermore, the configuration of the present embodiment also produces the effect that the nebulizer gas which obliquely hits the bottom surface of the injection container body 19 stirs the solution collected at the bottom of the container body 19 and thereby promotes its vaporization. By appropriately designing the angle and position of the blower tube 47, height of the container body 19 as well as other dimensions, the nebulizer gas can be made to hit the central area of the bottom surface, whereby the solution collected at the bottom will be more efficiently dispersed. FIG. 5A is one example of the relevant dimensions of the injection container 21 designed to make the nebulizer gas hit the central area of the bottom surface. According to the shown design, the nebulizer gas obliquely hits a point at a distance of 0.2 mm from the center of the bottom surface.

The Reynolds number has been calculated for a flow of the nebulizer gas supplied using the injection container 21 shown in FIG. 5A, with the gas flow rate, mean velocity, kinetic viscosity, and inner diameter of the blower tube assumed as in the table of FIG. 5B. As shown in the table, the Reynolds number in the present example was Re=2245572 and greater than the critical Reynolds number, Rec=2320. A Reynolds number (Re) which is greater than the critical Reynolds number (Rec) as in the present case means that the nebulizer gas spouted from the blower tube 47 becomes a turbulent flow.

In FIGS. 2A-5B, the length of the branch tube 42 is designed so that the projecting section 40A protrudes from the outlet portion 46. FIGS. 6A and 6B show another possible configuration, in which the length of the branch tube 42 is designed so that the projecting section 40A is hidden within the outlet portion 46. This structure of the branch tube 42 protects the inner tube 40 from exposure to the inner space of the injection container 21 and thereby prevents the droplets and powder scattered within the injection container 21 from being adhered to the inner tube 40. The droplets and powder cannot also be adhered to the outer tube 41, since this tube is not inserted into the injection container 21. Accordingly, the problem of contamination will not occur when a different liquid sample is injected into the next injection container.

Instead of increasing the length of the branch tube 42 as in the previous description to hide the projecting section 40A within the outlet portion 46, the length of the projecting section 40A may be decreased so as to hide the projecting section 40A within the outlet portion 46 without changing the length of the branch tube 42.

Figure 7A:
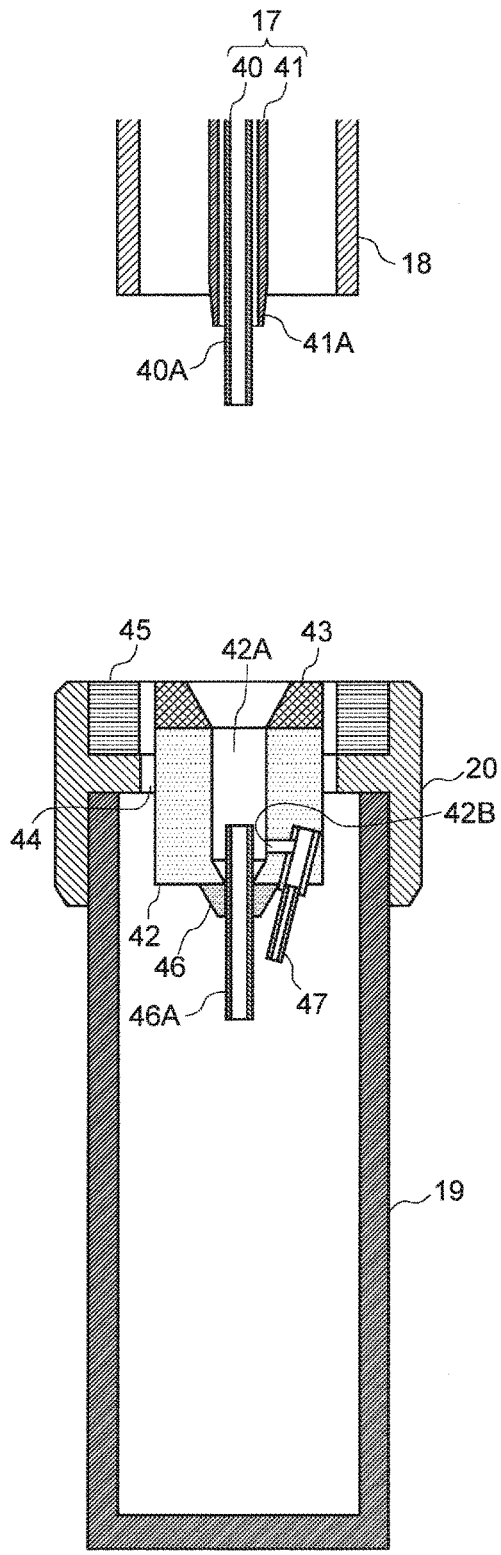
FIGS. 7A and 7B are schematic vertical sectional views of the sample introduction tube and the injection container in the gas-spouting liquid-sample injector according to another variation of the embodiment, where
Figure 7B:
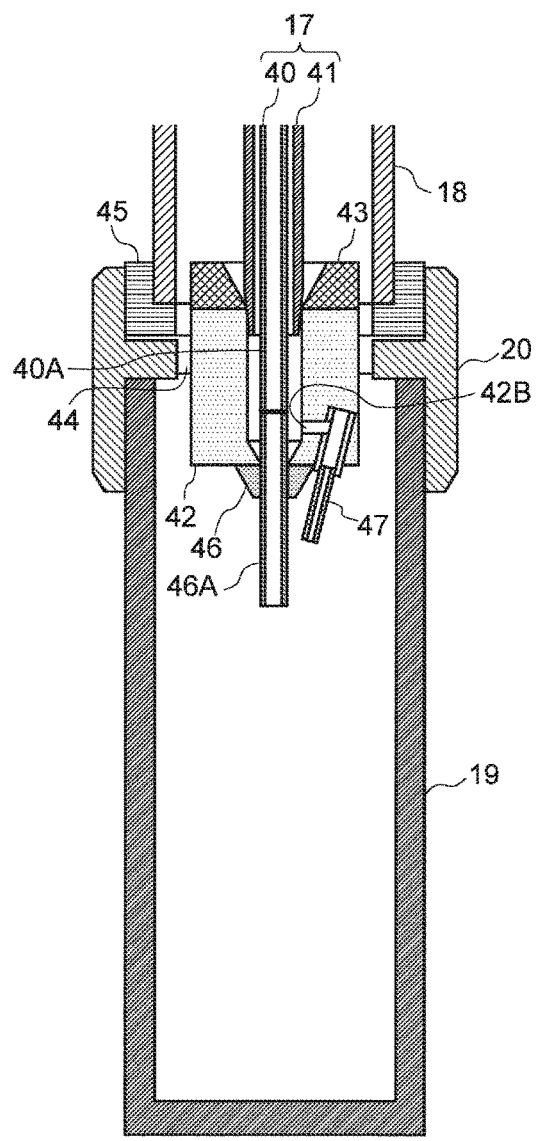
Figure 8A:
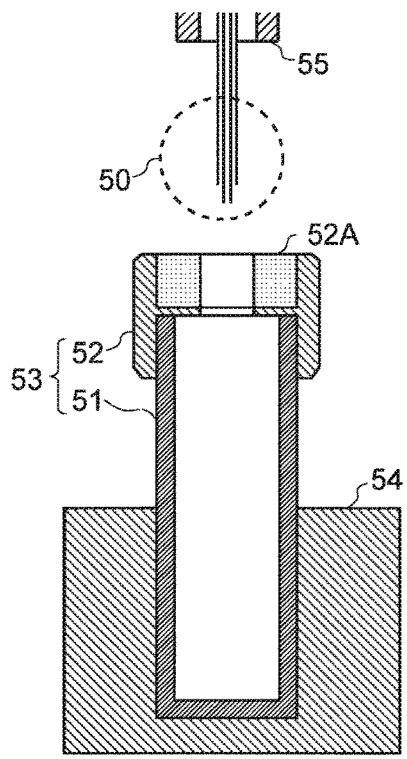
FIGS. 8A-8D are diagrams illustrating a powder production process by a conventional preparative separation-purification process.
Figure 8B:
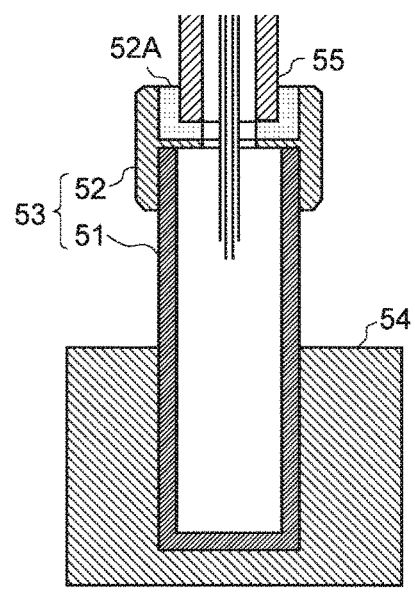
Figure 8C:
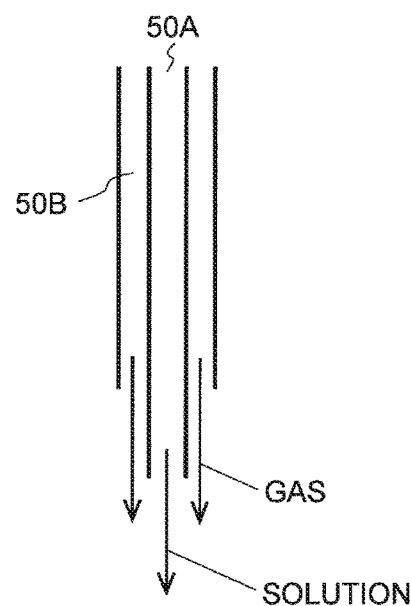
Figure 8D:
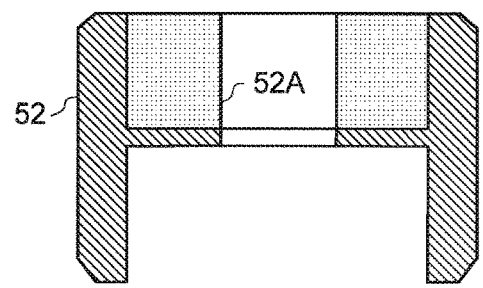

If the inner tube 40 is made of a PTFE resin material, the projecting section 40A of the inner tube 40 may be worn out due to the repeated insertion and removal of the projecting section 40A into and from the outlet portion 46 of the cover part 20. A solution to this problem is shown in FIGS. 7A and 7B, in which the lengths of the branch tube 42 and the inner tube 40 are designed so that the projecting section 40A of the inner tube 40 will stay within the main line 42A when the sample introduction tube 17 is inserted into the branch tube 42. Additionally, a cylindrical sleeve part 46A is attached to the outlet portion 46 of the branch tube 42. The length of this sleeve part 46A is designed so that the lower end of the projecting section 40A of the inner tube 40 is positioned close to the upper end of the sleeve part 46A when the sample introduction tube 17 is inserted into the branch tube 42. By this configuration, the projecting section 40A can be prevented from being worn out, since the projecting section 40A does not come in contact with the outlet portion 46 when the sample introduction tube 17 is inserted into the branch tube 42.

In the previously described configuration, the inner tube 40 may be made of stainless steel, whereas the sleeve part 46A should preferably be made of PTFE for the previously explained reason. The sleeve part 46A may be bent so that its lower end is slightly inclined toward the side where the blower tube 47 is located. Such a configuration reduces the amount of solution staying at the tip of the sleeve part 46A, and thereby improves the state of the powder to be obtained within the injection container 21.

The state of the powder to be obtained can also be controlled by changing the length of the sleeve part 46A, by obliquely cutting the tip of the sleeve part 46A, and/or by various other methods instead of, or in addition to, the bending of the sleeve part 46A.

It should be naturally understood that the previously described embodiment of the injection container as well as the gas-spouting liquid-sample injector according to the present invention can be appropriately changed or modified within the spirit of the present invention.

REFERENCE SIGNS LIST

1 . . . Solution Container
2 . . . Pure Water Container
3 . . . Eluting Solvent Container
4 . . . Switching Valve
5, 10, 11, 12, 13, 14, 22 . . . Passage
6 . . . Liquid-Sending Pump
7 . . . Switching Valve
8 . . . Trap Column
9 . . . Column Rack
15 . . . Switching Valve
16 . . . Fraction Collector Head
17 . . . Sample Introduction Tube
   40 . . . Inner Tube
      41 . . . Outer Tube
         41A . . . Lower End Portion
18 . . . Sealed Exhaust Tube
19 . . . Injection Container Body
20 . . . Cover Part
21 . . . Injection Container
23 . . . Gas Supplier
   23A . . . Proportional Valve
   23B . . . Gas Cylinder
24 . . . Container Rack
25 . . . Heater
26 . . . Temperature Sensor
27 . . . Temperature-Control Block
28 . . . Temperature Controller
29 . . . XYZ Drive Mechanism
30 . . . Controller
31 . . . Operation Unit
42 . . . Branch Tube
   42A . . . Main Line
   42B . . . Bypass Line
43 . . . Inlet Portion
44 . . . Exhaust Opening
45 . . . Cushion
46 . . . Outlet Portion
   46A . . . Sleeve Part
47 . . . Blower Tube

The invention claimed is:

1. An injection container for a liquid-sample injector equipped with a sample introduction tube composed of an outer tube for a nebulizer gas and an inner tube for a liquid, the inner tube having a projecting section protruding downward from a lower end of the outer tube, the injection container configured to be supplied with a mist of liquid sample from the sample introduction tube, and the injection container comprising:
   an injection container body with an upper opening;
   a cover part to be attached to the opening;
   a branch tube provided so as to penetrate the cover part, having a main line allowing an insertion of the sample introduction tube and a bypass line branched from the main line, the main line having an inner diameter larger than an outer diameter of the inner tube;
   an inlet portion provided at an upper end of the main line, having a structure for making gas-tight contact with the lower end of the outer tube;
   an outlet portion provided at a lower end of the main line, having a structure for making gas-tight contact with an outer circumferential surface of the inner tube; and
   a blower tube extending from a lower end of the bypass line toward an area below the outlet portion of the main line.

2. The injection container according to claim 1, wherein a position and/or a direction of a tip of the blower tube is variable.

3. A gas-spouting liquid-sample injector, comprising:
   a sample introduction tube for supplying a liquid sample in a mist form into an injection container, the sample introduction tube composed of an outer tube for a nebulizer gas and an inner tube for a liquid, the inner tube having a projecting section protruding downward from a lower end of the outer tube;
   a branch tube provided in the injection container, having a main line allowing an insertion of the sample introduction tube and a bypass line branched from the main line, the main line having an inner diameter larger than an outer diameter of the inner tube;
   an inlet portion provided at an upper end of the main line, having a structure for making gas-tight contact with the lower end of the outer tube;
   an outlet portion provided at a lower end of the main line, having a structure for making gas-tight contact with an outer circumferential surface of the inner tube; and a blower tube extending from a lower end of the bypass line toward an area below the outlet portion of the main line.

4. The gas-spouting liquid-sample injector according to claim 3, further comprising a heater for heating the injection container.

5. The gas-spouting liquid-sample injector according to claim 3, wherein a position and/or a direction of a tip of the blower tube is variable.

6. The gas-spouting liquid-sample injector according to claim 5, further comprising a heater for heating the injection container.

\* \* \* \* \*